US00PP08534P

United States Patent [19]

Chiamori et al.

[11] Patent Number: Plant 8,534

[45] Date of Patent: Jan. 11, 1994

[54] "SUNNY RED" NECTARINE TREE

[76] Inventors: Patrick Chiamori, 9588 S. Lac Jac, Reedley, Calif. 93654; Stuart R. Hirasuna, 5421 N. Sequoia Ave., Fresno, Calif. 93711

[21] Appl. No.: 964,877

[22] Filed: Oct. 22, 1992

[51] Int. Cl.[5] ..... A01H 5/00

[52] U.S. Cl. ..... Plt./41.1

[58] Field of Search ..... Plt. 41.1, 41.3, 43.1

*Primary Examiner*—James R. Feyrer

*Assistant Examiner*—Erich E. Veitenheimer

*Attorney, Agent, or Firm*—Worrel & Worrel

[57] ABSTRACT

A new and distinct variety of nectarine tree which is somewhat remotely similar to the "Red Jim" nectarine tree (U.S. Plant Pat. No. 4,518) from which it was derived, but from which it is distinguished by producing fruit which are mature for harvesting and shipment approximately ten days after the fruit produced by the "Red Jim" nectarine tree.

1 Drawing Sheet

BACKGROUND OF THE NEW VARIETY

The present invention relates to a new and distinct variety of nectarine tree, which will hereinafter be denominated varietally as the "Sunny Red" nectarine tree, and more particularly to a nectarine tree which produces fruit which are mature for harvesting and shipment approximately August 28 to September 9 in the San Joaquin Valley of central Calif., and which further is distinguished by its large size and high skin coloration.

The commercial success of the "Red Jim" nectarine tree (U.S. Plant Pat. No. 4,518) has resulted in efforts directed toward the discovery of new nectarine varieties possessing many of the same attributes, but ripening for harvest in different time periods. For example, the "Late Red Jim II" nectarine tree (U.S. Plant Pat. No. 7,505) ripens for harvest approximately August 30 through September 20 in the San Joaquin Valley of central Calif. There is however, a potential demand for additional new varieties having other characteristics to varying degrees similar to those of the "Red Jim" nectarine tree. Not surprisingly, many of the new varieties so discovered are mutations of the "Red Jim" nectarine tree. Thus, distinctions in fruit size, skin coloration, flesh coloration, flavor and the like may be of substantial commercial significance where the fruit otherwise is comparable to that of the "Red Jim" nectarine tree. The new variety of nectarine tree of the present invention possesses a combination of attributes which are believed to make it a promising candidate in these regards.

ORIGIN AND ASEXUAL REPRODUCTION OF THE NEW VARIETY

The present variety of nectarine tree hereof was discovered by the inventors in an orchard belonging to Patrick Chiamori which is located on Newmark Avenue in Parlier in the San Joaquin Valley of central Calif. The applicants discovered the seedling in Septemper, 1989 as a mutation of the "Red Jim" nectarine tree. The new variety was asexually reproduced at the inventor's direction in February, 1990 and the progeny of the new variety planted in the same orchard located in Parlier. The inventors closely observed the asexually reproduced trees of the new variety from that time. In 1991, the progeny of the new variety bore fruit and in September of the same year, the inventors confirmed that the progeny possessed characteristics identical to those of the parent.

SUMMARY OF THE NEW VARIETY

The "Sunny Red" nectarine tree is characterized as to novelty by producing a clingstone fruit with a blush coloration which has dark garnet red spotting and striping. Further the fruit produced by the "Sunny Red" nectarine tree is ripe for commercial harvesting and shipment approximately August 28 to September 9 in the San Joaquin Valley of central Calif. The new variety is most closely similar to the "Red Jim" nectarine tree (U.S. Plant Pat. No. 4,518) from which it was derived as a mutation, but from which it is distinguished by producing fruit which are ripe for harvesting and shipment approximately ten days after the "Red Jim" nectarine tree, the fruit further characterized by a more glossy skin and a greater tendency for a red blush coloration in a stripped pattern as compared with that of the fruit of the "Red Jim" nectarine tree.

BRIEF DESCRIPTION OF THE DRAWING

The accompanying drawing is a color photograph of six mature nectarines of the instant variety showing the form and coloration thereof, a first disposed in side elevation; a second disposed in side elevation; a third sectioned to expose the pit cavity and with the stone removed therefrom; a fourth disposed in side elevation so as to expose the suture thereof; a fifth disposed to expose the base thereof; and a sixth oriented so as to expose the apex thereof; a stone of the instant variety disposed in side elevation; and representative foliage of the new variety.

DETAILED DESCRIPTION

Referring more specifically to the pomological details of this new and distinct variety of nectarine tree, the following has been observed under the ecological conditions prevailing at the orchard of origin which is located in Parlier, Calif. All major color code designations are by reference to the *Dictionary of Color,* by Maerz and Paul, Second Edition, 1950. Common color names are also occasionally employed.

TREE

Generally: Upright-spreading with eventual tree form and density determined by pruning. The tree is hardy as grown under typical central San Joaquin Valley climatic conditions.

*Productivity.*—Productive.

*Regularity of bearing.*—Regular.

Trunk:

*Size.*—Average diameter.

*Surface texture.*—Average surface texture for the species.

*Color.*—Grey (7-A-9) with some hues of brown present.

*Lenticels — numbers.*—Numerous moderately large lenticels are present on the trunk with lenticel openings surrounded by brown (14-C-11) callous tissue.

*Lenticels — size.*—Moderately large.

Branches:

*Size.*—Average.

*Surface texture.*—Average for the species.

*Color.*—One year or older wood — Chestnut brown (7-E-11).

*Color.*—Immature branches — Light green (20-K-5) with red pigmentation on shoots exposed to direct sunlight.

Surface Texture.—Immature growth — Current season's shoots have a smooth surface texture.

LEAVES

Size:

Generally.—Medium to large. Leaf measurements have been taken from leaves growing near midpoint of vigorous current seasons's shoots.

*Average length.*—Average 18.4 mm (0.724 inches) including the petiole.

*Average width.*—Average 4.6 mm (0.181 inches).

Form: Lanceolate with acuminate leaf tip. Leaf tip usually twisted to one side.

Color:

*Upwardly disposed surface.*—Medium green (23-L-7).

*Downwardly disposed surface.*—Grey-green (22-J-6).

*Leaf vein.*—Midvein on lower leaf surface is a yellow-green (19-K-4).

Marginal form:

*Generally.*—Margins crenate with individual crenations rather low and wide.

Leaf margin: Moderately undulate.

Petiole:

*Size.*—Medium.

*Length.*—Average 11 mm (0.433 inches).

*Thickness.*—Average 1.5 mm (0.059 inches) to 2.0 mm (0.079 inches).

*Color.*—Yellow-green (19-K-4), slightly more green along the petiole groove.

Stem glands:

*Form.*—Reniform.

*Position.*—Most commonly 3 to 4 glands present.

*Pattern.*—Two located on the basal margin of the leaf blade and one to two present in alternate position upon the leaf petiole.

*Color.*—Shiny green-yellow (19-L-5), darkening and deteriorating with age.

Stipules: Two small stipules present, subtending young leaves. Stipules are early deciduous.

*Color.*—Light green (18-I-7).

FLOWERS

Flower buds:

*Size.*—Average.

*Color.*—Bud scales a dark brown (7-J-11).

*Form.*—Conic and the buds are covered with an abundance of grey pubescence.

Flowers:

*Generally.*—Bloom was observed on mature grafted tree of the new variety in March of 1990 in an orchard near Parlier, Calif. Number of chilling hours accumulated in the general Fresno County fruit growing district during the 1989–1990 winter season was well over 1300. This number of hours at or below 45 degrees Fahrenheit represents a colder than average winter chilling season.

Date of bloom: Medium to slightly late in relation to the bloom of other common commercial nectarine varieties. Bloom is about 3 days later than that of the "Red Jim" nectarine tree. Date of full bloom for the new variety was Mar. 17 in 1990.

Size:

Generally.—Large, showy type flower. Diameter of fully expanded bloom is 32 mm (1.26 inches) to 36 mm (1.42 inches).

Petals:

*Color.*—Young petals are light pink (1-D-1), darkening to a deeper pink (1-F-2), especially in the basal area of the petal claw.

*Size.*—Large.

*Length.*—18 mm (0.071 inches) to 21 mm (0.827 inches).

*Width.*—13 mm (0.512 inches) to 15 mm (0.591 inches).

*Form.*—Generally ovate.

*Claw.*—Form — Broadly truncate.

*Margin.*—Strongly undulate along the margins and especially apically.

Petal:

*Apex.*—Rounded.

Pedicel:

*Length.*—Medium, averaging 2.0 mm (0.079 inches).

*Thickness.*—1.5 mm (0.059 inches).

*Color.*—Shiny green (18-L-6).

Nectaries:

*Color.*—Bright orange (10-D-12) when young, becoming more dull with age.

Anthers:

*Size.*—Medium.

Pollen — Abundant.

*Color.*—Yellow (10-J-5).

Stamens:

*Length.*—Averages from 15 mm (0.591 inches) to 18 mm (0.709 inches).

The stamens are generally longer than the flower pistil.

Filament:

Color.—Light pink (1-C-7), darkening with age to a violet (2-I-2).

Pistil:

*Length.*—13 mm (0.512 inches) to 16 mm (0.630 inches), including the ovary.

*Color.*—Light green (18-E-2).

*Surface.*—Pistil and ovary surfaces are glabrous.

Bloom quantity: Average in bloom density. One to two flower buds present per node, most commonly two.

FRUIT

Maturity when described: Ripe for commercial harvesting and shipment approximately Aug. 28 to Sep. 9, 1989 in Parlier in the San Joaquin Valley of central Calif.

Size:

*Generally.*—Uniform, large.

*Average cheek diameter.*—73 mm (2.87 inches).

*Average suture diameter.*—72 mm (2.83 inches).

*Average axial diameter.*—74 mm (2.91 inches).

Form:

*Uniformity.*—Uniform, slightly asymmetrical.

Symmetry.—Ovate to almost globose in lateral aspect. Most frequently nearly globose in apical aspect.

Suture:

*Generally.*—A broad groove from apex to base, narrowing within the stem cavity. The suture takes on the underlying ground or blush coloration of the fruit. Usually some narrow striping is present along the suture line in the darker red (6-K-11) color range. The ventral suture is distinct over the apical shoulder with some suture depression also on the dorsal suture side of the apex.

Ventral surface:

*Generally.*—Rounded and only slightly lipped. One side usually protrudes slightly more than the other.

Stem cavity:

*Generally.*—Medium to slightly small.

*Depth.*—Moderately deep.

*Shape.*—Oval to almost globose. The basal shoulders of many fruit show an indentation where the fruit was pressed against the bearing branch.

Stem:

*Generally.*—Medium to slightly short in length.

*Length.*—Average range from 11 mm (0.433 inches) to 13 mm (0.051 inches).

*Thickness.*—3 mm (0.118 inches) to 4 mm (0.157 inches).

*Color.*—Yellow-green (18-K-3).

Base: Generally rounded. Base angle somewhat variable, but base most commonly slightly oblique to the fruit axis.

Apex:

*Shape.*—Generally rounded with only a very low tip. More specifically, the fruit of the "Sunny Red" nectarine tree of the present invention has an apex form which is unlike the "Red Jim," "Olympia," and "Late Red Jim" nectarine trees. The apexes of the fruit of these varieties are each described as having a recessed tip, or a tip that lies below the level of the fruit apical shoulder. The "Sunny Red" nectarine tree is also dissimilar to that of the "Olympia" nectarine tree in that the fruit of the "Olympia" is described as having a pistil point which is "not evident," whereas the fruit of the "Sunny Red" nectarine tree has a pistil point that is present and slightly oblique to the fruit axis. The "Late Red Jim II" nectarine tree produces fruit which has variability in apex form from rounded to slightly pointed, whereas the fruit of the "Sunny Red" nectarine tree has a quite uniform apex form with rounded apical shoulders, but with a uniform low tip which is almost always slightly raised above the apical shoulders.

Pistil point: Slightly oblique.

Skin:

*Generally.*—Thickness — Average. Glabrous. Tenacious to flesh at commercial maturity.

*Flavor.*—Mild.

*Texture.*—Bright, glossy finish on skin.

*Tendency to crank.*—None observed.

*Blush color.*—Ranges from an orange-red (5-K-11) to a darker red (6-K-11), with a range of intensities in between. Variable from 30 percent to 75 percent of fruit surface, depending on degree of exposure to direct sunlight. Most blush areas are overlain with red spotting and striping in a dark garnet red intensity range (7-L-8). In a high percentage of fruit, the dark red mottle and striping are very distinct.

*Ground color.*—Yellow-amber (10-K-4).

*Flesh color.*—Interior coloration of the flesh from the skin inward to about half way to the stone is a yellow-amber (9-K-2).

*Surface of pit cavity.*—Very dark red (8-L-6), shading to a lighter red (6-L-10) as the red color radiates out from the stone area and tunrs progressively lighter. This coloration pattern is very similar to that of the "Red Jim," "Olympia," "Late Red Jim," and "Late Red Jim II" nectarine trees. This characteristic would reasonably be similar in the four genetically related clingstone varieties "Red Jim," "Late Red Jim," "Late Red Jim II," and "Sunny Red." Other late season clingstone varieties such as "Royal Giant" and "Olympia" also exhibit the pattern of very dark red/maroon coloration in the pit well and radiating into the flesh. This very dark pit well coloration is so common in late season clingstone nectarines that it could only rarely be used as a distinguishing characteristic.

*Flavor.*—Good, slightly acidic.

*Aroma.*—Slight.

*Texture.*—At commercial maturity the flesh is firm and crisp, softening somewhat with advancing maturity.

*Fibers.*—Numbers — Moderate number of short, ligth colored fibers present.

*Ripening.*—Ripens evenly.

*Eating quality.*—Good.

Stone:

*Attachment.*—Clingstone. Stone tightly held in cavity.

*Fibers.*—Numbers — Numerous fibers attached to stone. Length — Moderately short.

*Size.*—Medium to slightly large. Length — Average 34 mm (1.339 inches) to 37 mm (1.457 inches). Width — Average 24 mm (0.945 inches) to 25 mm (0.098 inches). Thickness — Average 19 mm (0.748 inches) to 20 mm (0.787 inches).

*Form.*—Generally — Obovate.

*Apex.*—Shape — Generally rounded with a short, sharp, acute tip.

*Color.*—Dry — Light brown (14-D-9) accompanied by a moderate amount of purple staining.

*Sides.*—Generally — Variable, but most often slightly unequal in size.

*Base.*—Shape — Thick and broadly truncate. Base angle somewhat variable, from slightly oblique to right-angularly related to the stone axis.

*Hilum.*—Moderately large and very well defined. Margins of hilum surrounded by a thick, finely grooved collar.

*Surfaces.*—Lateral surfaces rather coarse with deep grooves especially apically, and along the ventral suture. Numerous deep pits present laterally.

*Ventral edge.*—Broad with several low wings converging apically

*Dorsal edge.*—Medium thickness, with a deep groove 1.0 mm (0.039 inches) to 1.5 mm (0.059 inches) in width extending from stone base to about mid-suture. The mid-suture area is characterized by several high, prominent ridges converging basally. The upper edge from the apex to 12 mm (0.472 inches) to 15 mm (0.591 inches) below the apex is moderately eroded and at times slightly concave.

*Tendency to split.*—None observed.

Use: Appropriate for both local fresh market and long distance shipping.

Keeping quality: Good.

Although the new variety of nectarine tree possesses the described characteristics noted above as a result of the growing conditions prevailing in Parlier, Calif. in the central part of the San Joaquin Valley of Calif., it is to be understood that variations of the usual magnitude and characteristics incident to changes in growing conditions, irrigation, fertilization, pruning and pest control are to be expected.

Having thus described and illustrated our new variety of nectarine tree, what we claim as new and desire to be secured by Plant Letters Patent is:

1. A new and distinct variety of nectarine tree substantially as illustrated and described and which is somewhat remotely similar to the "Red Jim" nectarine tree (U.S. Plant Pat. No. 4,518) from which it was derived and to the "Olympia" nectarine tree (U.S. Plant Pat. No. 6,248), but from which it is distinguished by producing fruit having an apex that can be characterized as generally rounded with a low tip which are mature for commercial harvesting and shipment approximately August 28 to September 9 approximately ten days later than the "Red Jim" nectarine tree in the San Joaquin Valley of central Calif. and which possesses a more glossy skin with more of a tendency for a red blush coloration in a stripped pattern and a pistil that is slightly oblique to the fruit axis.

* * * * *

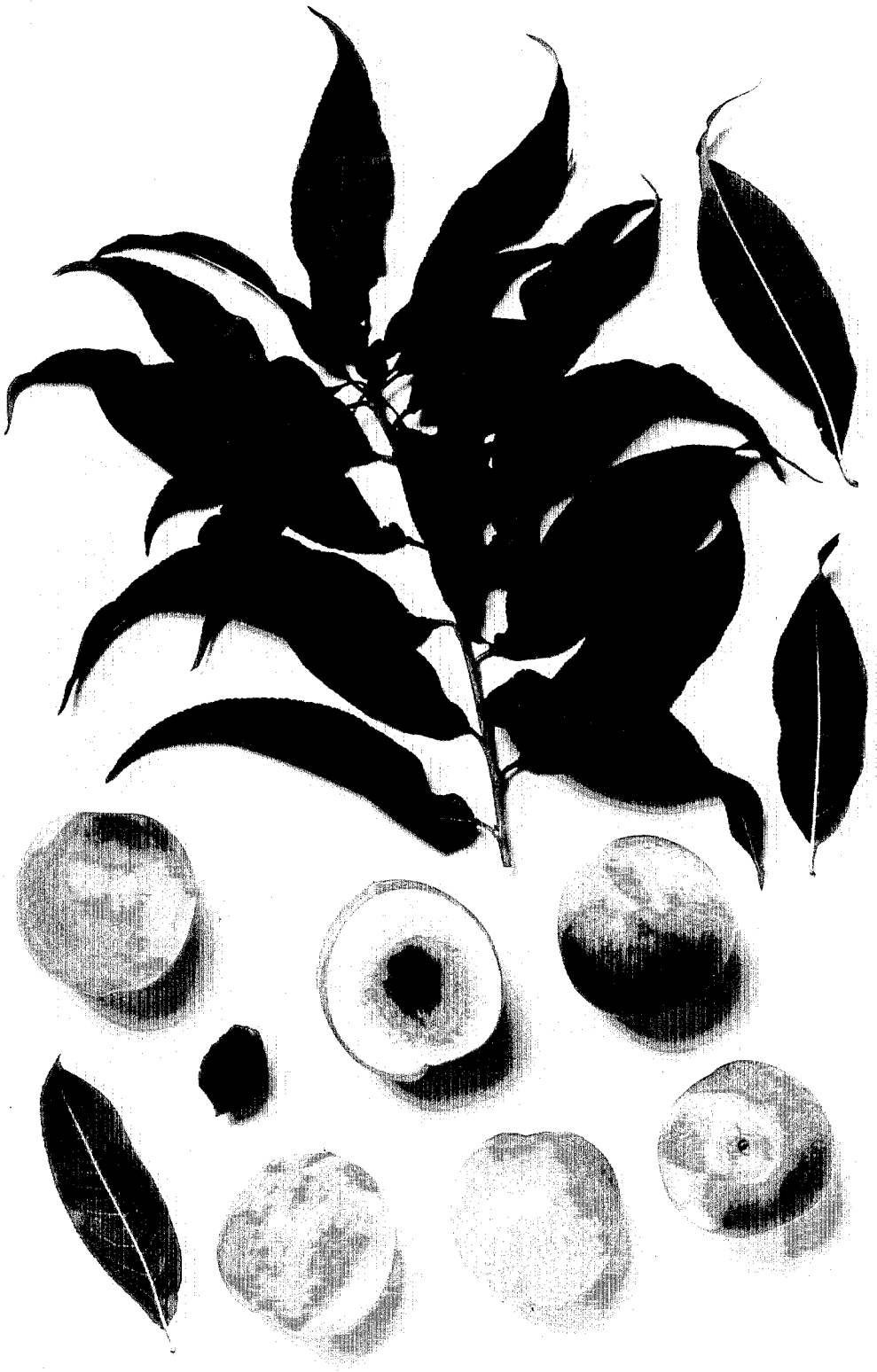

UNITED STATES PATENT AND TRADEMARK OFFICE

CERTIFICATE OF CORRECTION

PATENT NO. : PP 08,534

DATED : January 11, 1994

INVENTOR(S) : Patrick Chiamori, Stuart R. Hirasuna

It is certified that error appears in the above-identified patent and that said Letters Patent is hereby corrected as shown below:

Column 6, line 46, delete "ligth" and substitute ---light---.

Column 8, line 23, after "pistil" insert ---point---.

Signed and Sealed this

Seventeenth Day of May, 1994

Bruce Lehman

*Attest:*

BRUCE LEHMAN

*Attesting Officer*

*Commissioner of Patents and Trademarks*